United States Patent [19]

Haugwitz

[11] 4,312,990
[45] Jan. 26, 1982

[54] 1-MERCAPTOACYL-3-[(AMINOSULFONYL)PHENYL]-4,5-DIHYDRO-1H-PYRAZOLE-5-CARBOXYLIC ACID

[75] Inventor: Rudiger D. Haugwitz, Titusville, N.J.

[73] Assignee: E. R. Squibb & Sons, Inc., Princeton, N.J.

[21] Appl. No.: 186,110

[22] Filed: Sep. 11, 1980

[51] Int. Cl.$^3$ .......................................... C07D 231/06
[52] U.S. Cl. ................................. 548/379; 424/273 P
[58] Field of Search ........................................ 548/379

[56] References Cited

U.S. PATENT DOCUMENTS 4,211,786  7/1980  Rovnyak .......................... 548/379

FOREIGN PATENT DOCUMENTS 879158  4/1980  Belgium .

Primary Examiner—Henry R. Jiles
Assistant Examiner—Natalia Harkaway
Attorney, Agent, or Firm—Lawrence S. Levinson; Donald J. Barrack

[57] ABSTRACT

Compounds having the formula

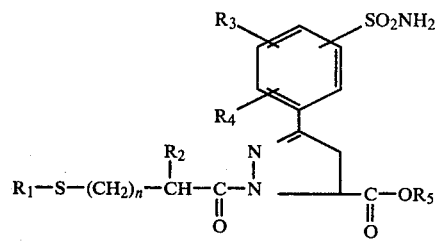

wherein
$R_1$ is hydrogen, alkyl, aryl, arylalkyl or a hydrolyzable acyl protecting group;
$R_2$ is hydrogen, alkyl or trifluoromethyl;
$R_3$ and $R_4$ each is independently hydrogen, halogen, trifluoromethyl, alkylamino, furylmethylamino, phenylamino, thienylmethylamino, alkoxy, aryloxy, benzylthio, arylthio, benzyl, benzoyl, hydroxy, cyano or arylmethoxy;
$R_5$ is hydrogen, alkyl or arylalkyl; and
n is 0, 1 or 2, have hypotensive activity.

8 Claims, No Drawings

1-MERCAPTOACYL-3-[(AMINOSULFONYL)PHENYL]-4,5-DIHYDRO-1H-PYRAZOLE-5-CARBOXYLIC ACID

RELATED APPLICATIONS

U.S. patent application Ser. No. 88,425, filed Oct. 25, 1979, now U.S. Pat. No. 4,254,267, issued Mar. 3, 1981, discloses compounds that inhibit the action of angiotensin converting enzyme in mammals and that are useful for the treatment of hypertension in mammals. The compounds have the formula

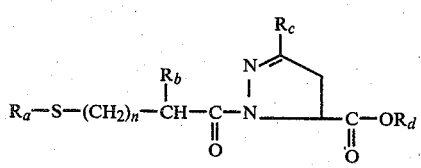

wherein $R_a$ is hydrogen, alkyl, aryl, arylalkyl or

wherein $R_e$ is alkyl or aryl; $R_b$ is hydrogen, alkyl, or haloalkyl; $R_c$ is furanyl, thienyl or pyridyl; $R_d$ is hydrogen, alkyl or arylalkyl; and n is 0, 1 or 2.

U.S. patent application Ser. No. 136,842, filed Apr. 3, 1980 discloses S-acylation products of mercaptoacyl amino acids and diuretics containing a carboxyl group. The compounds have both angiotensin converting enzyme inhibitory action and diuretic activity. Among the diuretics disclosed as useful for forming the compounds are 5-(aminosulfonyl)-2-[(2-furanylmethyl)amino]-4-(phenyloxy)benzoic acid and 5-(aminosulfonyl)-4-(benzoyl)-3-[(3-thienylmethyl)oxy]benzoic acid.

BACKGROUND OF THE INVENTION

The recent literature contains many disclosures of mercaptoacyl amino acids that inhibit the action of angiotensin converting enzyme in mammals and that are useful for the treatment of hypertension. One such reference is U.S. Pat. No. 4,211,786, issued July 8, 1980. This patent discloses compounds having the formula

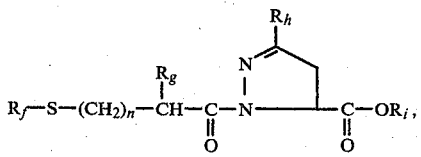

and basic salts thereof, wherein: $R_f$ is hydrogen, alkyl, aryl, arylalkyl or

wherein $R_j$ is alkyl or aryl; $R_g$ is hydrogen or alkyl; $R_h$ is aryl; $R_i$ is hydrogen, alkyl or arylalkyl; and n is 0, 1 or 2.

A second reference is Belgian Pat. No. 879,158. This patent discloses compounds having the formula

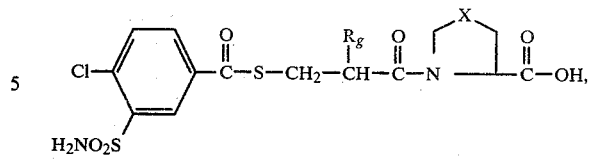

and salts thereof, wherein $R_g$ is hydrogen or alkyl and X is methylene or sulfur.

BRIEF DESCRIPTION OF THE INVENTION

Compounds having the formula

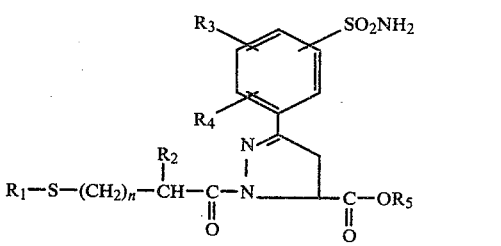

are hypotensive agents. In formula I, and throughout the specification, the symbols are as defined below.

$R_1$ is hydrogen, alkyl, aryl, arylalkyl or a hydrolyzable acyl protecting group such as alkylcarbonyl or arylcarbonyl;

$R_2$ is hydrogen, alkyl or trifluoromethyl;

$R_3$ and $R_4$ each is independently hydrogen, halogen, trifluoromethyl, alkylamino, furylmethylamino, phenylamino, thienylmethylamino, alkoxy, aryloxy, benzylthio, arylthio, benzyl, benzoyl, hydroxy, cyano or arylmethoxy;

$R_5$ is hydrogen, alkyl or arylalkyl; and n is 0, 1 or 2.

The term "aryl", as used throughout the specification either by itself or as part of a larger group, refers to phenyl or phenyl substituted with one, two or three halogen, alkyl, alkoxy, hydroxy, alkylcarbonyl, nitro, amino, alkylamino, dialkylamino, trifluoromethyl, cyano or carboxyl groups. Phenyl and monosubstituted phenyl are the preferred aryl groups, and phenyl is most preferred.

The term "alkyl", as used throughout the specification either by itself or as part of a larger group, refers to groups having 1 to 8 carbon atoms. Alkyl groups having 1 to 3 carbon atoms are preferred.

The term "alkoxy", as used throughout the specification either by itself or as part of a larger group, refers to groups having 1 to 8 carbon atoms. Alkoxy groups having 1 to 3 carbon atoms are preferred.

The term "halogen", as used throughout the specification either by itself or as part of a larger group, refers to fluorine, chlorine, bromine and iodine. The preferred halogen groups are chlorine and bromine.

DETAILED DESCRIPTION OF THE INVENTION

The compounds of formula I are useful as hypotensive agents. They inhibit the conversion of the decapeptide angiotensin I to angiotensin II and, therefore, are useful in reducing or relieving angiotensin related hypertension. The action of the enzyme renin on angiotensinogen, pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., humans. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one or a combination of the compounds of this invention, angiotensin dependent hypertension in the species of mammal (e.g., humans) suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 300 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methychlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture or compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Various synthetic routes are available for the preparation of the compounds of this invention. According to one preferred method, an acid or ester having the formula

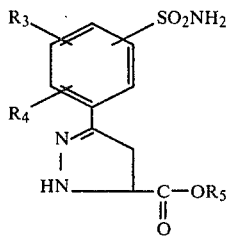

is coupled with an alkanoic acid having the formula

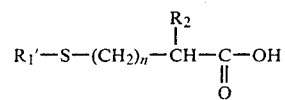

to yield a compound having the formula

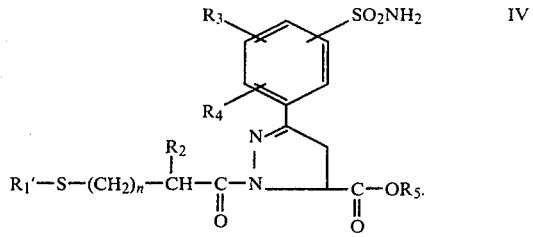

In formulas III and IV, and throughout the specification, the symbol $R_1'$ represents any $R_1$ group other than hydrogen. The coupling of an acid of formula III and an amino acid or amino acid ester of formula II can be accomplished using known amide bond forming procedures that are conventionally used in peptide syntheses. The reaction can be run in the presence of a coupling agent such as dicyclohexylcarbodiimide, or the acid can be activated by formation of its mixed anhydride, symmetrical anhydride, acid halide (preferably acid chloride) or acid ester, or by the use of Woodward reagent K, or N-ethoxycarbonyl-2-ethoxy-1,2-dihydroquinoline or the like. A review of these methods can be found in *Methoden der Organischen Chemie* (Houben-Weyl), Vol. XV, part II, page 1 et seq. (1974).

The compounds of formula I wherein $R_1$ is hydrogen can be obtained by deprotection of the sulfhydryl group of the corresponding compound of formula IV. Deprotection of a compound of formula IV wherein $R_1'$ is alkylcarbonyl or arylcarbonyl can be accomplished by treating the protected compound with aqueous ammonia, preferably in an oxygen-free atmosphere.

The compounds of formula II can be obtained using as a starting material acetophenones having the formula

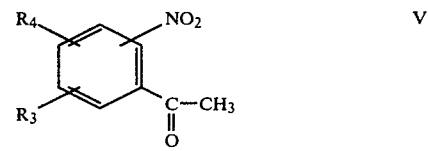

Methods for the synthesis of substituted acetophenones are described in *Methoden der Organischen Chemie* (Houben-Weyl), Ketone, Part I, page 15 et seq. (1974).

A nitro derivative of formula V can be reduced to the corresponding amino compound having the formula

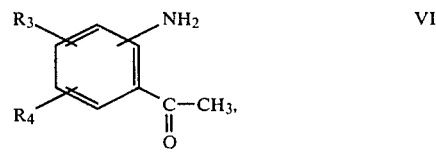

using procedures well-known in the art; e.g., a chemical reducing agent such as stannous chloride. Conversion of the amino group to a sulfonyl group can be accomplished by diazotization of a compound of formula VI, cupric halide catalyzed reaction with sulfur dioxide, and reaction with ammonia, ammonium carbonate or the like. The product has the formula

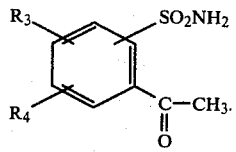

Reaction of an acetophenone of formula VII with glyoxylic acid, or ester thereof, preferably under acid conditions, yields a compound having the formula

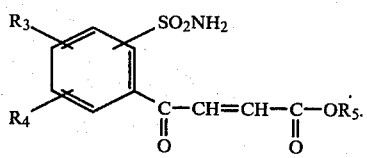

Cyclization of a compound of formula VIII with hydrazine using alkaline conditions yields the ring closed compound of formula II.

The compounds of formula I each contains at least one asymmetric carbon atom and accordingly exist in stereoisomeric forms or in racemic mixtures thereof. The above described synthesis can utilize the racemate or one of the enantiomers as starting material. When the racemic starting material is used in the synthetic procedure, the stereoisomers obtained in the product can be separated by conventional fractional crystallization of the diastereomeric salt mixture formed, e.g., with an optically active amine. It is theorized that the activity of the racemic products is due mostly to the L-isomer with respect to the carbon of the amino acid, and this isomer is accordingly preferred.

The following examples are specific embodiments of this invention.

EXAMPLE 1

(±)-3-[4-(Aminosulfonyl)phenyl]-4,5-dihydro-1-(3-mercapto-1-oxopropyl)-1H-pyrazole-5-carboxylic acid (A) p-Acetylbenzenesulfonamide A warmed solution of 54 g (0.4 mole) of p-aminoacetophenone in 280 ml of concentrated HCl and 40 ml of water is cooled to 0° C. and a solution of 28 g of $NaNO_2$ in 160 ml of water is added over 0.5 hour. The reaction mixture is stirred at 0° C. for an additional 0.25 hour and then poured cautiously into a well-stirred mixture of 6.0 g of $CuCl_2$ in 500 ml of acetic acid saturated with $SO_2$ at 0° C. When the foaming ceases (approx. 1 hour) the mixture is poured into 2 liters of ice water. The resulting solid is filtered off, washed with water and warmed with excess $(NH_4)_2CO_3$ to give a solid. Crystallization from aqueous ethanol yields 44.3 g of the title compound, melting point 177°–178° C.

(B) 5-[4-(Aminosulfonyl)phenyl]-4-oxo-2-pentenoic acid

A mixture of 37 g of p-acetylbenzenesulfonamide, 78.4 g of glyoxylic acid hydrate, 20 ml of 80% $H_2SO_4$ and 180 ml of dioxane is refluxed for 24 hours. An additional 10 g of glyoxylic acid hydrate is added and the mixture is refluxed for 24 hours. The reaction mixture is poured into 2 liters of water and extracted with ether. The organic layers are combined, dried, and evaporated to leave a solid which is crystallized from acetonitrile yielding 10.9 g of the title compound, melting point 180°–181° C.

(C) (±)-3-[4-(Aminosulfonyl)phenyl]-4,5-dihydropyrazole-5-carboxylic acid

A mixture of 12.75 g of 5-[4-(aminosulfonyl)phenyl]-4-oxo-2-pentenoic acid, 2.24 g of hydrazine and 3.0 g of KOH in 100 ml of methanol is refluxed for 3 hours, cooled, and 50 ml of methanol is removed in vacuo. Then there is added 50 ml of water and the mixture is acidified with concentrated HCl. The resulting solid is filtered off, washed with water, then ethanol and dried to yield 8.8 g of the title compound, melting point 224°–226° C.

(D) (±)-1-[3-(Acetylthio)-1-oxopropyl]-3-[4-(aminosulfonyl)phenyl]-4,5-dihydro-1H-pyrazole-5-carboxylic acid To a solution of 8.07 g of (±)-3-[4-aminosulfonyl)-phenyl]-4,5-dihydropyrazole-5-carboxylic acid and 2.5 g of $NaHCO_3$ in 150 ml of water layered with 75 ml of ethyl acetate, there are added concurrently at 0° C. a solution of 5.0 g of 3-acetylthiopropionyl chloride in 25 ml of ethyl acetate and a solution of 2.5 g of $NaHCO_3$ in 25 ml of water to maintain a pH of 6.5–7.0. The mixture is stirred at room temperature for 2.5 hours. The ethyl acetate layer is discarded and the aqueous layer is extracted twice with ethyl acetate before the pH is lowered to pH 4 using concentrated HCl. The resulting oil is extracted with ethyl acetate. The organic layers are combined, dried ($MgSO_4$) and evaporated to give an oily solid which is crystallized from ethyl acetate to yield 8.8 g of the title compound, melting point 183°–185° C.

(E) (±)-3-[4-(Aminosulfonyl)phenyl]-4,5-dihydro-1-(3-mercapto-1-oxopropyl)-1H-pyrazole-5-carboxylic acid A cold solution of 30 ml of 6.5 N $NH_4OH$ is treated under argon with 7.0 g of (±)-1-[3-(acetylthio)-1-oxopropyl]-3-[4-(aminosulfonyl)-phenyl]-4,5-dihydro-1H-pyrazole-5-carboxylic acid. The mixture is stirred at room temperature for 1 hour and then acidified with concentrated HCl. The resulting oil is extracted with ethyl acetate. The organic layers are combined, washed with saturated sodium chloride solution, dried, and evaporated to give an oily solid which is crystallized from acetonitrile to yield 4.1 g of the compound, melting point 199°–200° C.

Analysis calc'd for $C_{13}H_{15}N_3O_5S_2.0.25$ mole MeCN: C, 44.10; H, 4.31; N, 12.39. Found: C, 43.84; H, 4.34; N, 12.54.

EXAMPLE 2

[1(S),5(±)]-3-[3-(Aminosulfonyl)-4-chlorophenyl]-4,5-dihydro-1-(3-mercapto-2-methyl-1-oxopropyl)-1H-pyrazole-5-carboxylic acid (A) 3-Amino-4-chloroacetophenone A mixture of 39.8 g of 4-chloro-3-nitroacetophenone and 136 g of $SnCl_2.2H_2O$ in 220 ml of concentrated HCl is stirred at room temperature for 0.5 hours. The reaction mixture warms spontaneously to 70° C. then cools. Toluene (200 ml) is added and the reaction mixture is made alkaline with 30% NaOH. Ether is added and the layers are separated. The aqueous layer is extracted twice more with ether, the organic layers are combined, dried, and evaporated. The solid residue is crystallized from benzene to yield 29.6 g of the title compound, melting point 104°–105° C.

(B) 4-Acetyl-2-chlorobenzenesulfonamide

A warmed solution of 25.4 g (0.15 mole) of 3-amino-4-chloroacetophenone in 105 ml of concentrated HCl and 15 ml of water is cooled to 0° C. and a solution of 10.5 g of NaNO$_2$ in 60 ml of water is added over 0.5 hours. The reaction mixture is stirred at 0° C. for an additional 0.25 hours and then poured cautiously into a well-stirred mixture of 2.25 g of CuCl$_2$ in 187.5 ml of acetic acid saturated with SO$_2$ at 0° C. When the foaming ceases (approximately 1.5 hour) the mixture is poured into 1 liter of ice water. The resulting solid is filtered off, washed with water and warmed with 20 g of (NH$_3$)$_2$CO$_3$ to give a solid. Crystallization from ethanol yields 11.9 g of the title compound, melting point 146°–148° C.

(C) 5-[3-(Aminosulfonyl)-4-chlorophenyl]-4-oxo-2-pentenoic acid

A mixture of 11.6 g of 4-acetyl-2-chlorobenzenesulfonamide, 4,6 g of glyoxylic acid hydrate, 45 ml of dioxane and 5 ml of 80% H$_2$SO$_4$ is refluxed for 24 hours. An additional 2.3 g of glyoxylic acid hydrate is added and the mixture is refluxed for an additional 24 hours. The reaction mixture is poured into 500 ml of water and extracted with ether. The organic layers are combined, dried, and evaporated to leave a solid which is crystallized from acetonitrile to yield 5.7 g of the title compound, melting point 217°–218° C.

(D) (±)-3-[3-(Aminosulfonyl)-4-chlorophenyl]-4,5-dihydropyrazole-5-carboxylic acid A mixture of 5.8 g of 5-[3(aminosulfonyl)-4-chlorophenyl]-4-oxo-2-pentenoic acid and 1.2 g of KOH in 50 ml of methanol is treated with 0.7 ml of hydrazine and the mixture is refluxed for 3 hours. Approximately 40 ml of methanol is removed in vacuo and 20 ml of water is added. The mixture is acidified to pH 6.5 with concentrated HCl and the resulting solid is filtered off and washed with ether to give 2.2 g of the title compound, melting point 125° C. dec.

(E) [1(S),5(±)]-1-[3-(Acetylthio)-2-methyl-1-oxopropyl]-3-[3-(aminosulfonyl)-4-chlorophenyl]-4,5-dihydro-1H-pyrazole-5-carboxylic acid To a solution of 2.0 g of (±)-3-[3-(aminosulfonyl)-4-chlorophenyl]-4,5-dihydropyrazole-5-carboxylic acid and 0.6 g of NaHCO$_3$ in 25 ml of water layered with 20 ml of ethyl acetate there are added concurrently a solution of 1.2 g of 3-acetylthiopropionyl chloride in 10 ml of ethyl acetate and a solution of 0.6 g of NaHCO$_3$ in 10 ml of water at 0° C. The mixture is stirred at room temperature for 2 hours. The ethyl acetate layer is discarded and the aqueous layer is extracted twice with ethyl acetate before the pH is lowered to pH 4 (HCl concentrated). The resulting oil is extracted with ethyl acetate and the organic layers are combined, dried (MgSO$_4$) and evaporated to give an oily solid which is redissolved in ethyl acetate and dicyclohexylamine is added. The resulting solid is filtered off, dissolved in ethyl acetate and water and 10% KHSO$_4$ is added. The layers are separated and the aqueous layer is extracted twice with ethyl acetate. The organic layers are combined, dried (MgSO$_4$) and evaporated to give 0.75 g of the title compound as a foam.

(F) [1(S),5(±)]-3-[3-(Aminosulfonyl)-4-chlorophenyl]-4,5-dihydro-1-(3-mercapto-2-methyl-1-oxopropyl)-1H-pyrazole-5-carboxylic acid A cold solution of 15 ml of 6.5 N NH$_4$OH was treated under argon with 0.7 g of [1(S),5(±)]-1-[3-(acetylthio)-2-methyl-1-oxopropyl]-3-[3-(aminosulfonyl)-4-chlorophenyl]-4,5-dihydro-1H-pyrazole-5-carboxylic acid. The mixture is stirred at room temperature for 1 hour and then acidified (pH 6) with concentrated HCl. The resulting oil is extracted with ethyl acetate. The organic layers are combined, washed with saturated NaCl, dried (MgSO$_4$) and evaporated to yield 0.48 g of the title compound as a foam.

Analysis calc'd for C$_{14}$H$_{16}$ClN$_3$O$_5$S$_2$: C, 41.43; H, 3.97; N, 10.35. Found: C, 41.82; H, 3.98; N, 10.05.

EXAMPLES 3–10

Following the procedure of Example 2, but substituting the compound listed in column I for 4-chloro-3-nitroacetophenone and the compound listed in column II for 3-acetylthiopropionyl chloride, yields the compound listed in column III.

| | Column I | Column II | Column III |
|---|---|---|---|
| 3. | 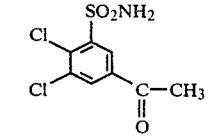 | 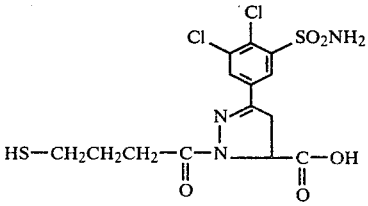 | 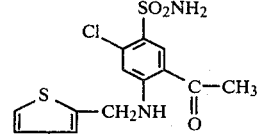 |
| 4. | 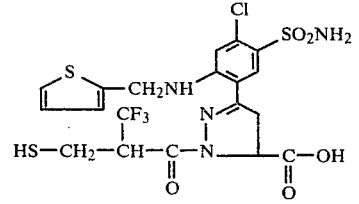 | | |

4,312,990
-continued
| Column I | Column II | Column III |
|---|---|---|
| 5. | | |
| 6. | | |
| 7. | | |
| 8. | | |
| 9. | | |
| 10. | | |
What is claimed is:
1. A compound having the formula
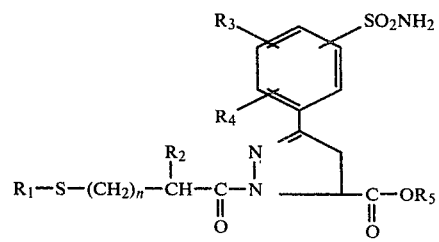
wherein $R_1$ is hydrogen, alkyl, aryl, arylalkyl, alkylcarbonyl or arylcarbonyl;

$R_2$ is hydrogen, alkyl or trifluoromethyl;

$R_3$ and $R_4$ each is independently hydrogen, halogen, trifluoromethyl, alkylamino, furylmethylamino, phenylamino, thienylmethylamino, alkoxy, aryloxy, benzylthio, arylthio, benzyl, benzoyl, hydroxy, cyano or arylmethoxy;

$R_5$ is hydrogen, alkyl or arylalkyl; and n is 0, 1 or 2;

wherein the term "aryl" refers to phenyl or phenyl substituted with one, two or three halogen, alkyl, alkoxy, hydroxy, alkylcarbonyl, nitro, amino, alkylamino, dialkylamino, trifluoromethyl, cyano or carboxyl groups; and the terms "alkyl" and "alkoxy" refer to groups having 1 to 8 carbon atoms.

2. A compound in accordance with claim 1 wherein $R_4$ is hydrogen.

3. A compound in accordance with claim 1 wherein $R_1$ is hydrogen.

4. A compound in accordance with claim 1 wherein $R_2$ is methyl.

5. A compound in accordance with claim 1 wherein n is 1.

6. A compound in accordance with claim 1 wherein $R_5$ is hydrogen.

7. The compound in accordance with claim 1 ($\pm$)-3-[4-(aminosulfonyl)phenyl]-4,5-dihydro-1-(3-mercapto-1-oxopropyl)-1H-pyrazole-5-carboxylic acid.

8. The compound in accordance with claim 1 [1(S),5($\pm$)]-3-[3-(aminosulfonyl)-4-chlorophenyl]-4,5-dihydro-1-(3-mercapto-2-methyl-1-oxopropyl)-1H-pyrazole-5-carboxylic acid.

* * * * *